(12) United States Patent
Yamamoto et al.

(10) Patent No.: US 8,064,061 B2
(45) Date of Patent: Nov. 22, 2011

(54) SAMPLE ANALYZER AND SAMPLE ANALYZING METHOD

(75) Inventors: Norimasa Yamamoto, Kobe (JP); Naohiko Matsuo, Kobe (JP); Takashi Yamato, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/730,225

(22) Filed: Mar. 30, 2007

(65) Prior Publication Data

US 2007/0229830 A1 Oct. 4, 2007

(30) Foreign Application Priority Data

Mar. 30, 2006 (JP) ................................. 2006-092792

(51) Int. Cl.
G01N 21/00 (2006.01)
G01N 21/25 (2006.01)
G01J 3/51 (2006.01)

(52) U.S. Cl. .......... 356/436; 356/414; 356/418; 422/63; 422/64

(58) Field of Classification Search .......... 356/432–439, 356/317–319, 410–418, 441–442; 422/63–67; 436/47–49
See application file for complete search history.

(56) References Cited

U.S. PATENT DOCUMENTS

| | | | |
|---|---|---|---|
| 3,609,042 A | 9/1971 | Yasuda et al. | |
| 4,208,353 A * | 6/1980 | Webster et al. | 502/245 |
| 4,313,735 A | 2/1982 | Yamashita et al. | |
| 4,451,433 A * | 5/1984 | Yamashita et al. | 422/63 |
| 4,528,159 A | 7/1985 | Liston | |
| 4,668,617 A | 5/1987 | Furuta et al. | |
| 4,684,252 A * | 8/1987 | Makiguchi et al. | 356/328 |
| 4,685,801 A | 8/1987 | Minekane | |
| 4,774,055 A * | 9/1988 | Wakatake et al. | 422/64 |
| 4,778,763 A * | 10/1988 | Makiguchi et al. | 436/47 |
| 4,896,963 A * | 1/1990 | Kato | 356/328 |
| 5,587,129 A * | 12/1996 | Kurosaki et al. | 422/64 |
| 5,698,450 A * | 12/1997 | Ringrose et al. | 436/526 |
| 5,734,468 A | 3/1998 | McNeal | |
| 6,353,471 B1 | 3/2002 | Samsoondar et al. | |
| 6,388,750 B1 * | 5/2002 | Liu et al. | 356/436 |
| 6,409,968 B1 * | 6/2002 | Takahashi | 422/64 |
| 6,797,518 B1 | 9/2004 | Jacobs et al. | |
| 2005/0259261 A1 * | 11/2005 | Harada et al. | 356/436 |
| 2007/0222973 A1 * | 9/2007 | Hoshiko et al. | 356/39 |
| 2008/0070318 A1 | 3/2008 | Yamamoto et al. | |

FOREIGN PATENT DOCUMENTS

| | | |
|---|---|---|
| EP | 0 355 738 B1 | 2/1990 |
| JP | 2-223859 A | 9/1990 |
| JP | 6-265554 A | 9/1994 |
| JP | 7-58263 B2 | 6/1995 |
| JP | 7-280814 A | 10/1995 |
| JP | 10-170444 A | 6/1998 |
| JP | 10-274656 A | 10/1998 |
| JP | 3229498 B2 | 9/2001 |
| WO | 98/21564 A | 5/1998 |

* cited by examiner

*Primary Examiner* — Sang Nguyen
(74) *Attorney, Agent, or Firm* — Sughrue Mion, PLLC

(57) ABSTRACT

A sample analyzer is disclosed that comprising: a light source section for emitting light; a first optical information acquiring section for illuminating a sample with the light emitted by the light source section, and for acquiring first optical information; and a second optical information acquiring section for illuminating a measurement specimen, to be prepared by adding a reagent to the sample, with the light emitted by the light source section, and for and acquiring second optical information. A sample analyzing method, intended for use in an automated sample analyzer, is also described.

21 Claims, 10 Drawing Sheets

SAMPLE ANALYZER AND SAMPLE ANALYZING METHOD

CROSS-REFERENCE TO RELATED APPLICATIONS

This application claims priority from Japanese Patent Application 2006-092792 filed on Mar. 30, 2006, the disclosure of which is herein incorporated by reference in its entirety.

FIELD OF THE INVENTION

The present invention relates to a sample analyzer and sample analyzing method, and specifically relates to a sample analyzer and sample analyzing method which use first optical information acquiring section and second optical information acquiring section.

BACKGROUND

Devices are known which measure the light absorption (optical information) of a serum sample (sample) using a probe (first optical information acquiring section), and thereafter optically measure the serum sample (main measurement) using clinical detection device (second optical information acquiring section) (for example, U.S. Pat. No. 5,734,468).

The device disclosed in U.S. Pat. No. 5,734,468 transports a serum sample that is measurable by a clinical analysis device to a clinical analysis device based on the light absorbance of the sample after having measured the light absorbance of the sample within a needle by illuminating a serum sample aspirated by the needle of a probe using light emitted from a light emitting diode. This device analyzes the existence of hemolysis, icteris, and lipemia a serum sample in a needle by illuminating the serum sample in a needle with light of five different wavelengths emitted from five light emitting diodes. When hemolysis, icteris or lipemia present in the serum sample exceeds a predetermined value, the probe is moved to a position corresponding to a waste container, and the serum sample aspirated in the needle is disposed of in the waste container. Conversely, when hemolysis, icteris or lipemia present in the serum sample is less than a predetermined value, the probe is moved to a position corresponding to a clinical analysis device, the serum sample aspirated in the needle is moved to a container of the clinical analysis device and optically measured (main measurement) by the clinical analysis device.

The device disclosed in U.S. Pat. No. 5,734,468 disadvantageously requires the provision of a light source separate from the five light emitting diodes for illuminating the serum sample within the needle of the probe when performing an optical measurement (main measurement) by the clinical analysis device. As a result, the size of the device is enlarged by the addition of the light source for performing the optical measurement by the clinical analysis device.

Moreover, when the light source for illuminating the serum sample accommodated in the container of the clinical analysis device is provided separately from the five light emitting diodes, light from that light source differs in quality from the light of the light emitting diodes that illuminate the serum sample within the needle of the probe, and that different quality light from that separate light source illuminates the serum sample in the container of the clinical analysis device. Therefore, the estimation as to whether or not to perform a measurement (main measurement) using the clinical analysis device must be completed based on the results of the measurements using light of different quality from that of the light used in the main measurement (probe measurement results). The reliability of such an estimation is not necessarily high. There is, therefore, a possibility that a sample that is measurable by the clinical analysis device may be disposed of prior to being moved to the clinical analysis device. As a result, there is less serum sample available for analysis in the main measurement.

SUMMARY

A first sample analyzer embodying features of the present invention includes: a light source section for emitting light; a first optical information acquiring section for illuminating a sample with the light emitted by the light source section, and for acquiring first optical information; and a second optical information acquiring section for illuminating a measurement specimen, to be prepared by adding a reagent to the sample, with the light emitted by the light source section, and for and acquiring second optical information.

A first sample analyzing method, intended for use in an automated sample analyzer, embodying features of the present invention includes steps of: (a) providing a sample at a predetermined position; (b) illuminating the sample with light emitted from a light source by using a light emitting device which has the light source, and acquiring first optical information from the sample; (c) preparing a measurement specimen by adding a reagent to the sample; (d) illuminating the measurement specimen with light emitted from the light source by using the light emitting device, and acquiring second optical information from the measurement specimen; (e) conducting an analysis of the characteristic of the sample based on the first optical information and second optical information; and (f) outputting a result of the analysis.

A second sample analyzing method, intended for use in an automated sample analyzer, embodying features of the present invention includes steps of: (a) providing a sample to a predetermined position; (b) illuminating the sample with light emitted from a light source by using a light emitting device which has a light source, and acquiring first optical information from the sample; (c) analyzing the first optical information and determining whether the analysis result is within a predetermined range; (d) preparing a measurement specimen by adding reagent to the sample when it has been determined in step (c) that the analysis result is within the predetermined range; (e) illuminating a measurement specimen with light emitted from a light source by using the light emitting device, and acquiring second optical information from the measurement specimen; (f) analyzing the characteristics of the sample based on the second optical information; and (g) outputting the result of the analysis of step (f).

DETAILED DESCRIPTION OF THE PREFERRED EMBODIMENTS

The embodiment of the present invention is described below based on the drawings.

Figure 1:
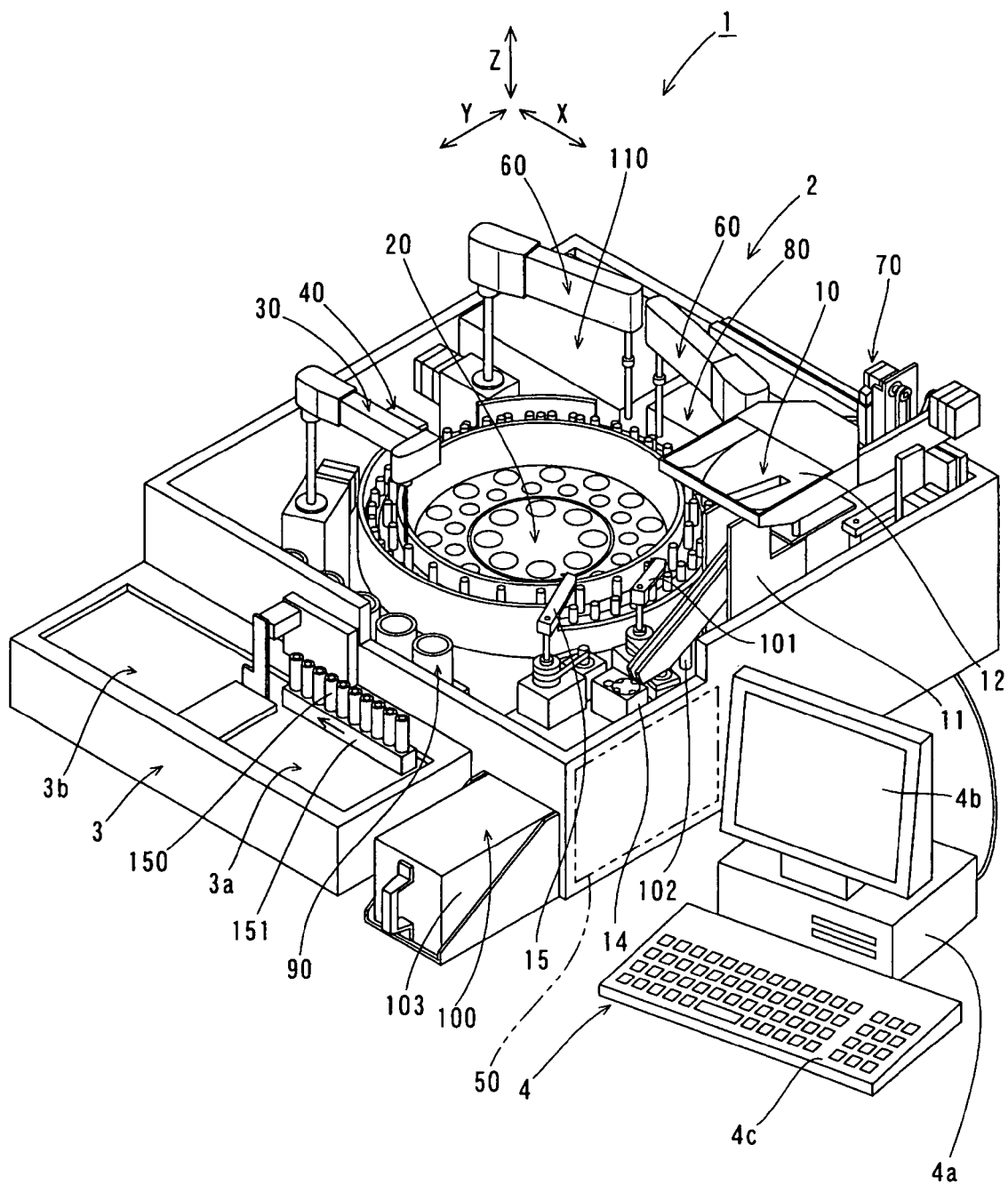
FIG. 1 is a perspective view showing the general structure of an embodiment of the sample analyzer of the present invention.
Figure 2:
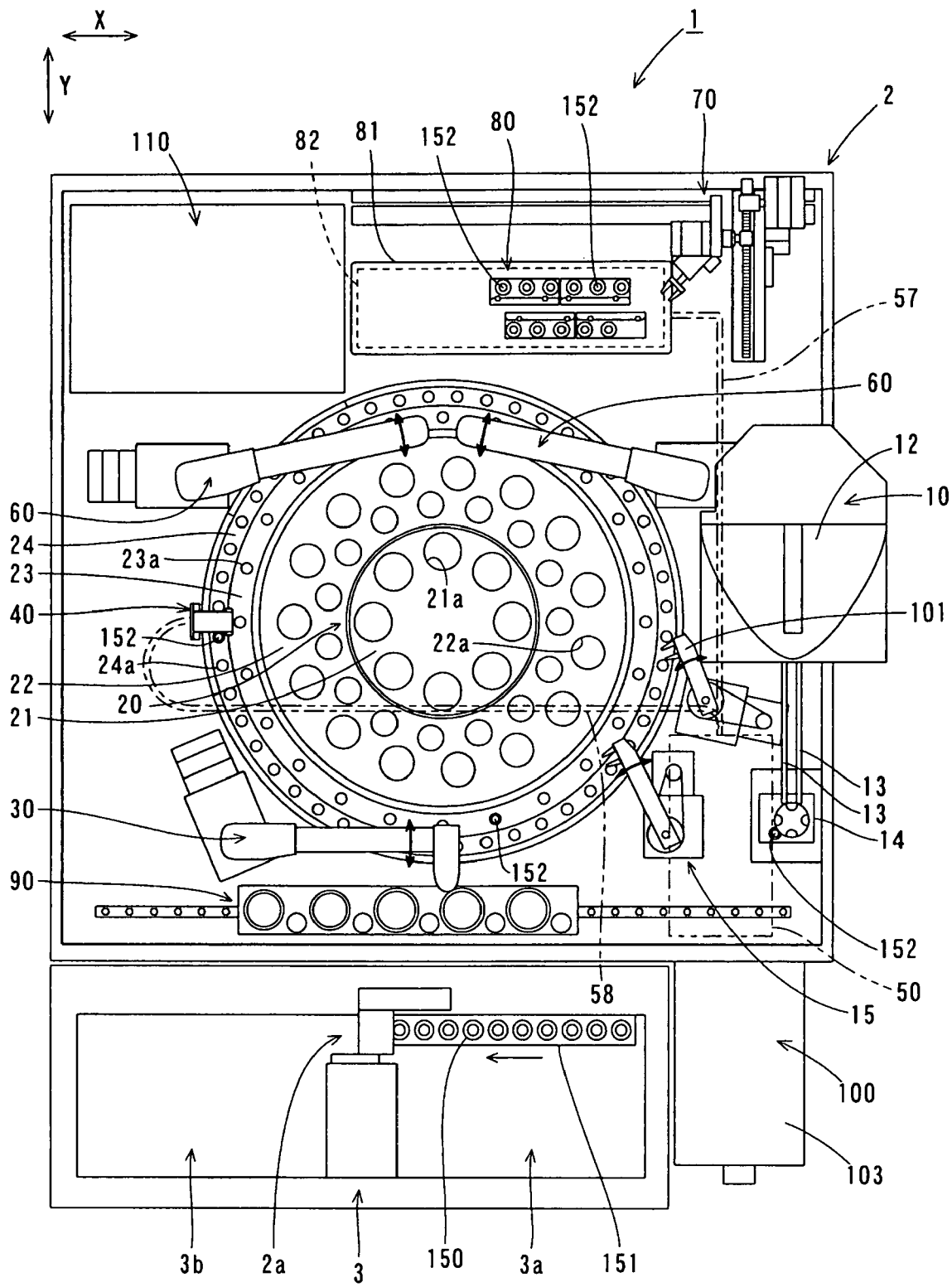
FIG. 2 is a plan view of the detection device and transport device of the sample analyzer of the embodiment in FIG. 1.
Figure 3:
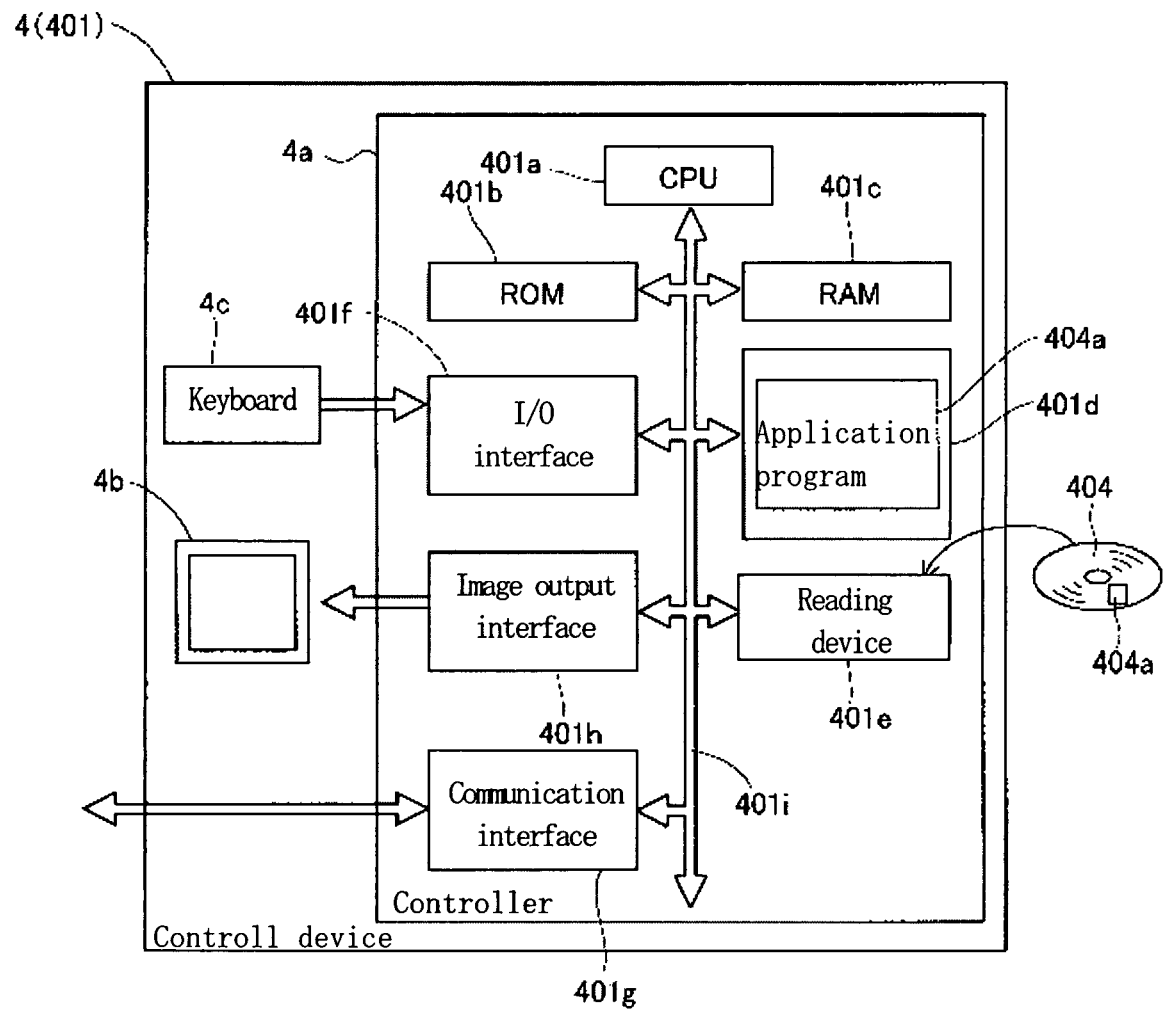
FIG. 3 is a block diagram of the control device of the sample analyzer of the embodiment in FIG. 1.
Figure 4:
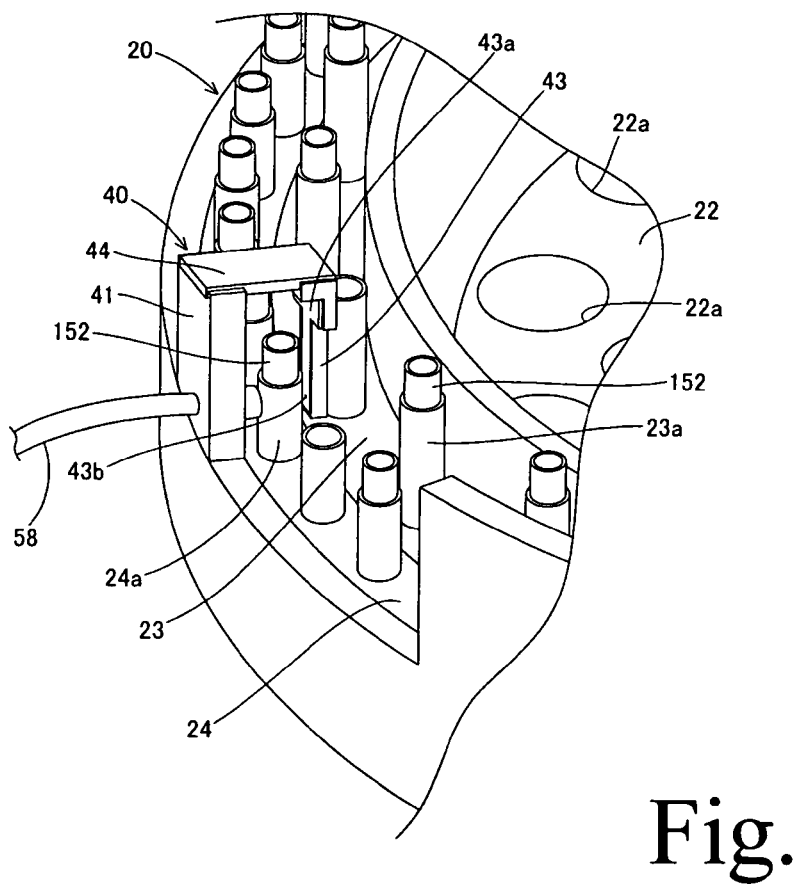
FIG. 4 is a perspective view of a first optical information acquiring section of the embodiment of the sample analyzer shown in FIG. 1.
Figure 5:
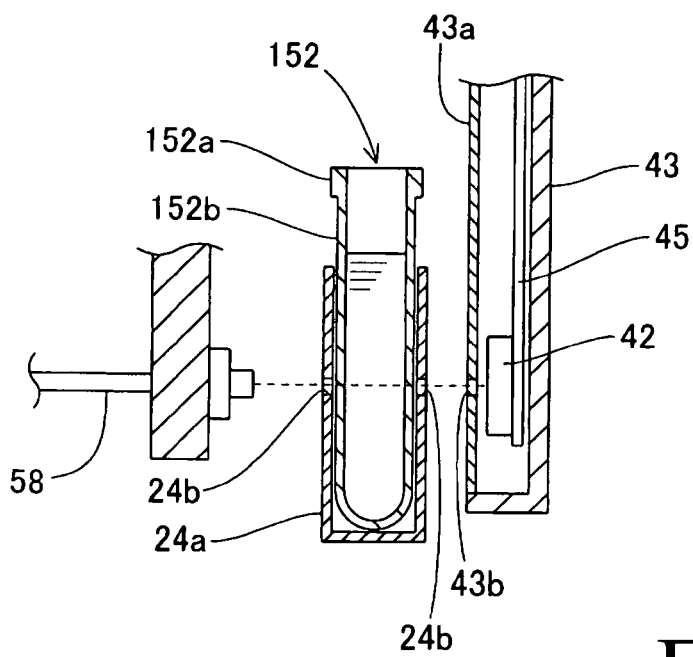
FIG. 5 is a schematic view of a first optical information acquiring section of the embodiment of the sample analyzer shown in FIG. 1.
Figure 6:
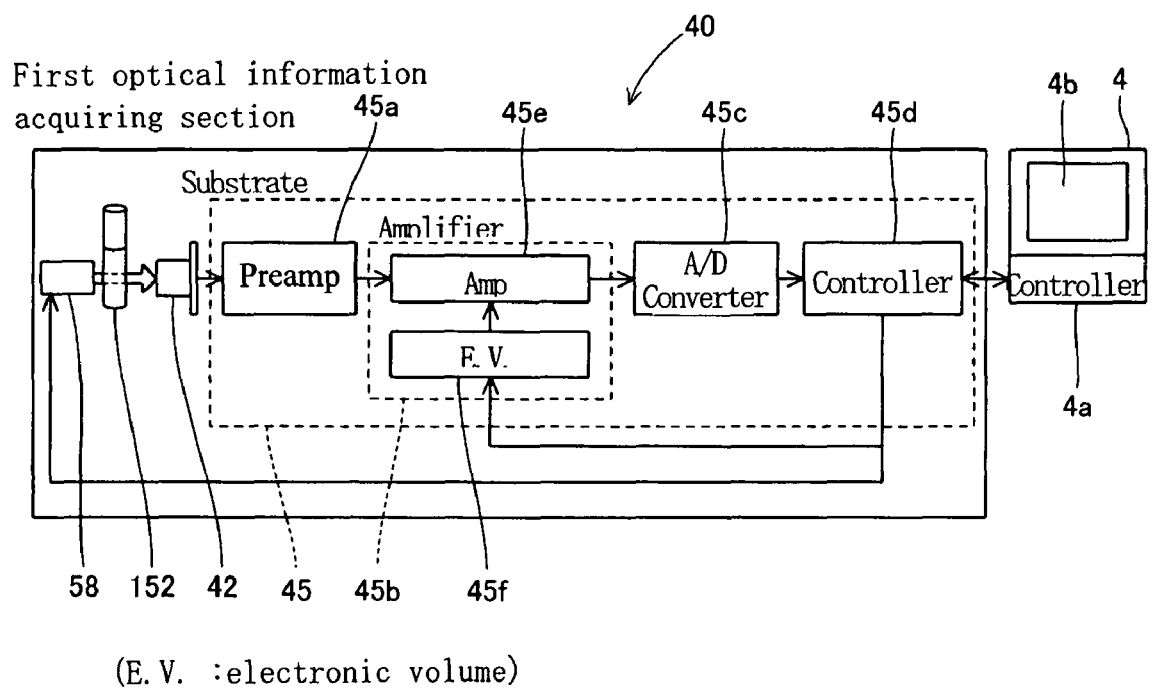
FIG. 6 is a block diagram of a first optical information acquiring section of the embodiment of the sample analyzer shown in FIG. 1.
Figure 7:
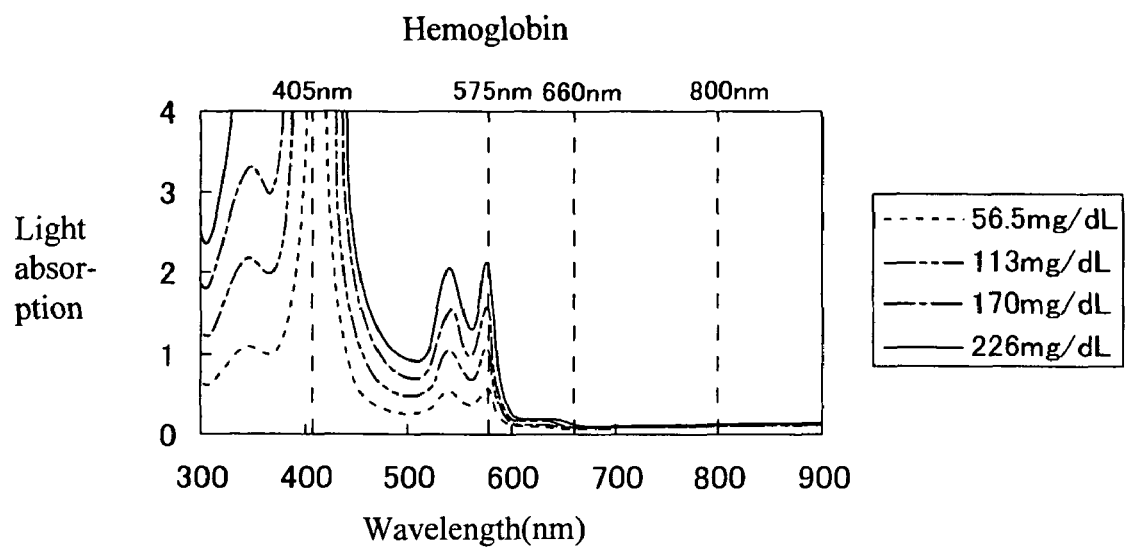
FIG. 7 is a graph of the light absorbance spectrum of interference substance (hemoglobin)
Figure 8:
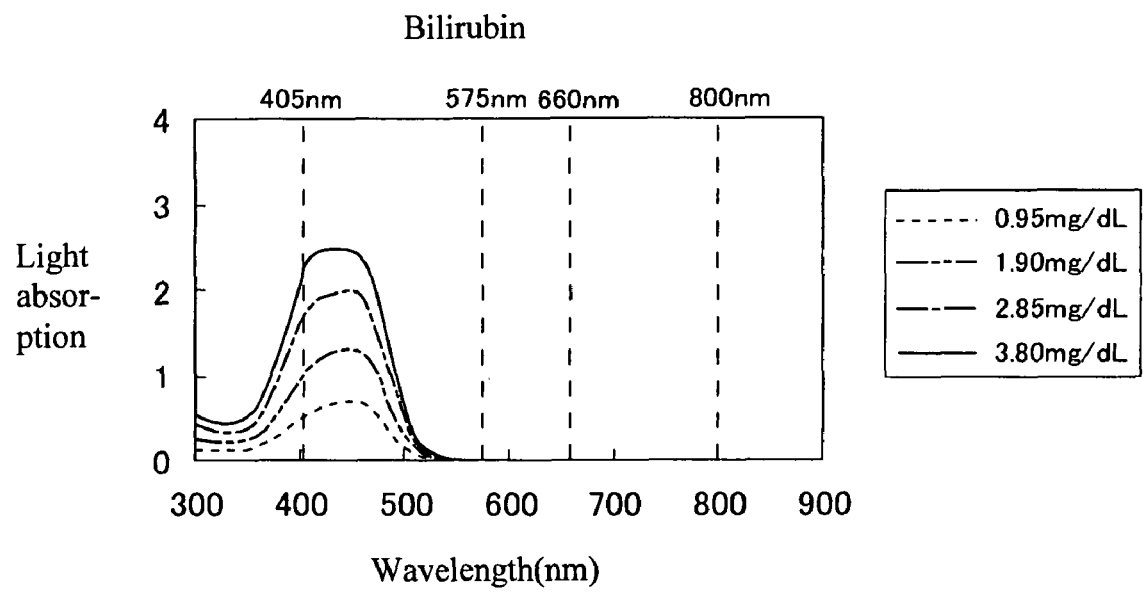
FIG. 8 is a graph of the light absorbance spectrum of interference substance (bilirubin)
Figure 9:
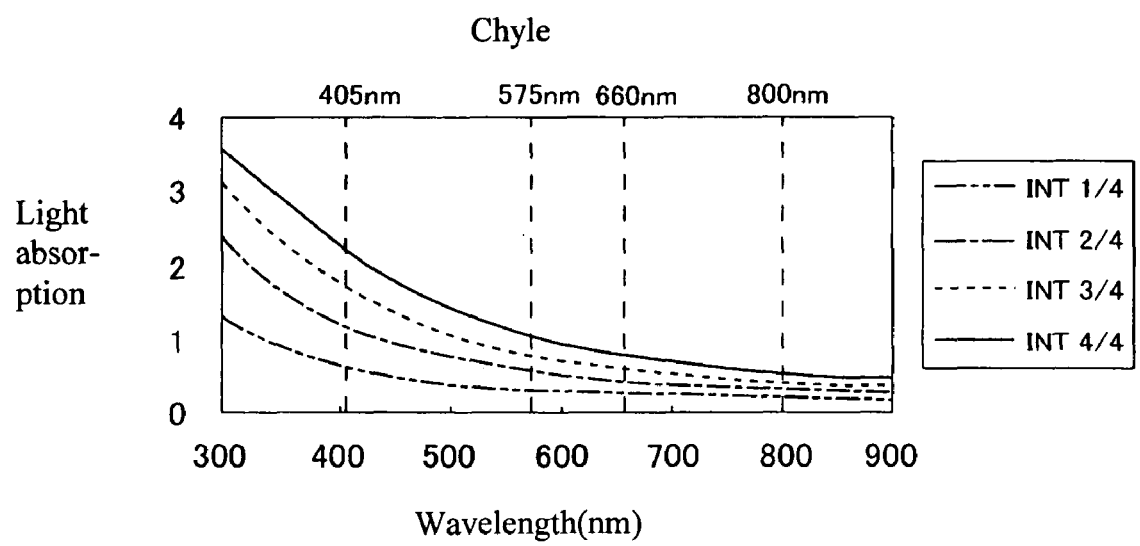
FIG. 9 is a graph showing the light absorbance spectrum of interference substance (chyle)
Figure 10:
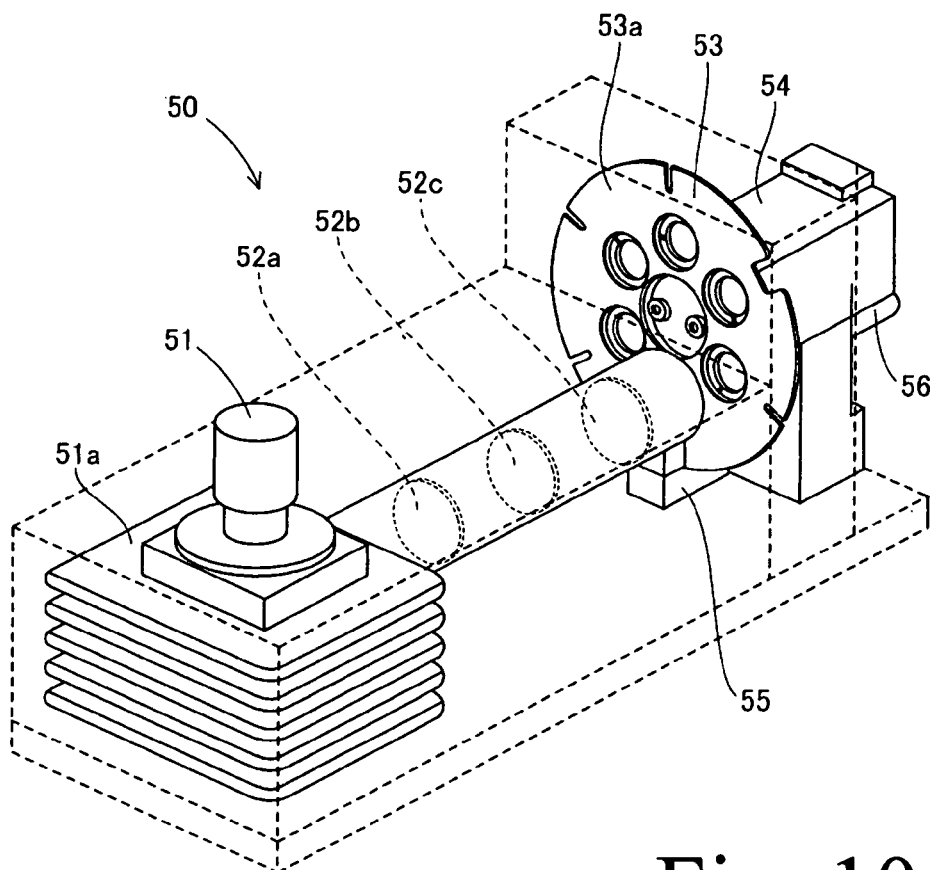
FIG. 10 is a perspective view of a lamp unit of the embodiment of the sample analyzer shown in FIG. 1.
Figure 11:
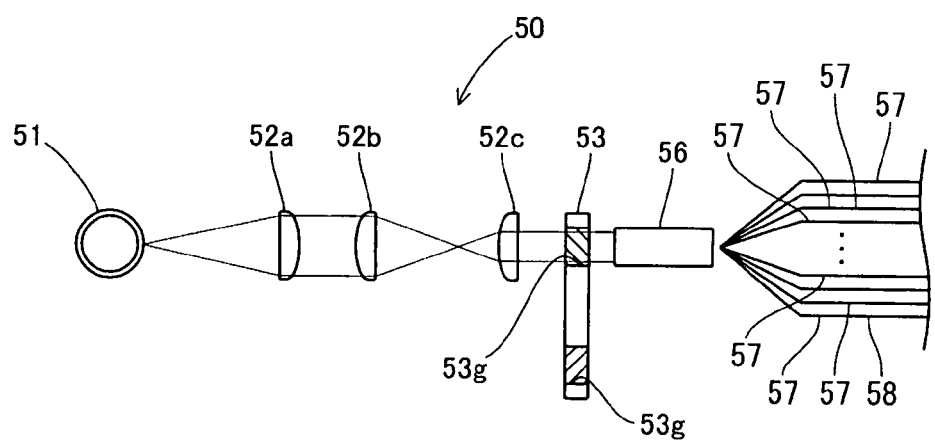
FIG. 11 is a schematic view of a lamp unit of the embodiment of the sample analyzer shown in FIG. 1.
Figure 12:
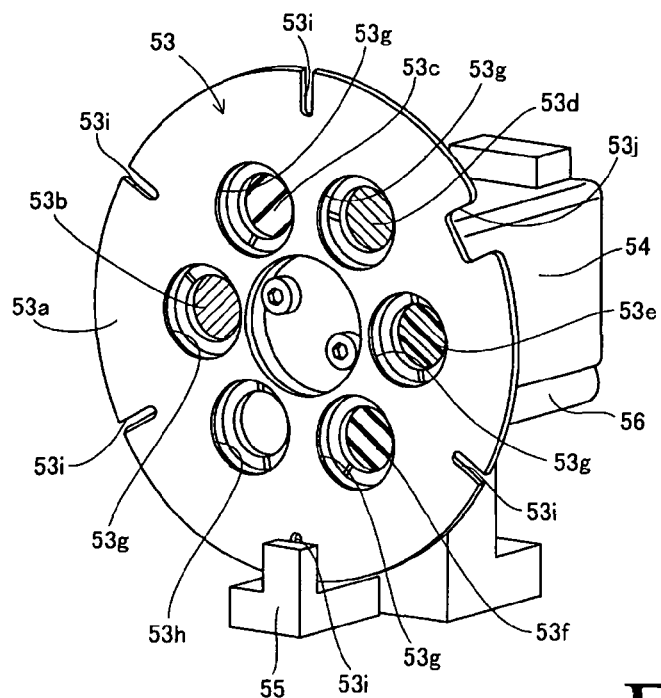
FIG. 12 is an enlarged perspective view showing the filter of the lamp unit in FIG. 10.
Figure 13:
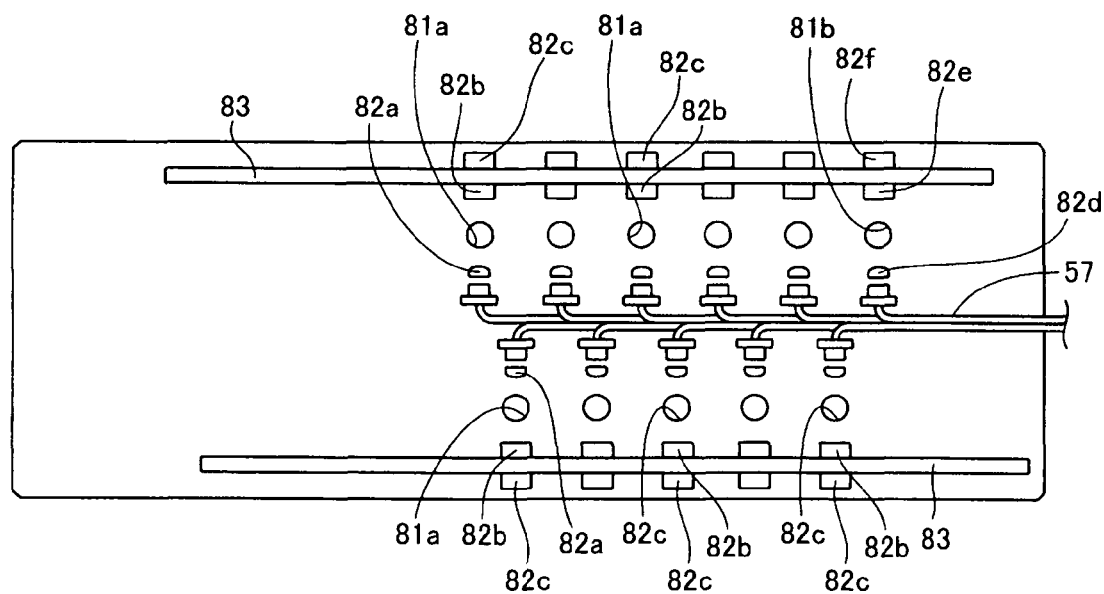
FIG. 13 is a brief view illustrating the internal structure of the detection section of a second optical information acquiring section of the embodiment of the sample analyzer shown in FIG. 1.
Figure 14:
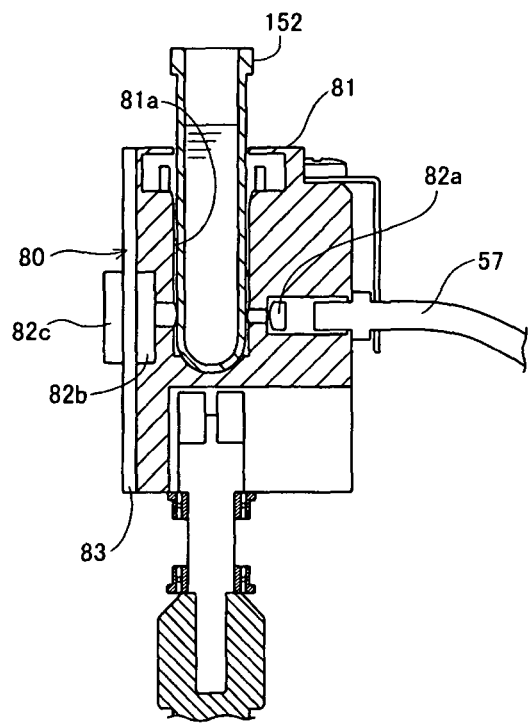
FIG. 14 is a section view illustrating the structure of the detection section of a second optical information acquiring section of the embodiment of the sample analyzer shown in FIG. 1.
Figure 15:
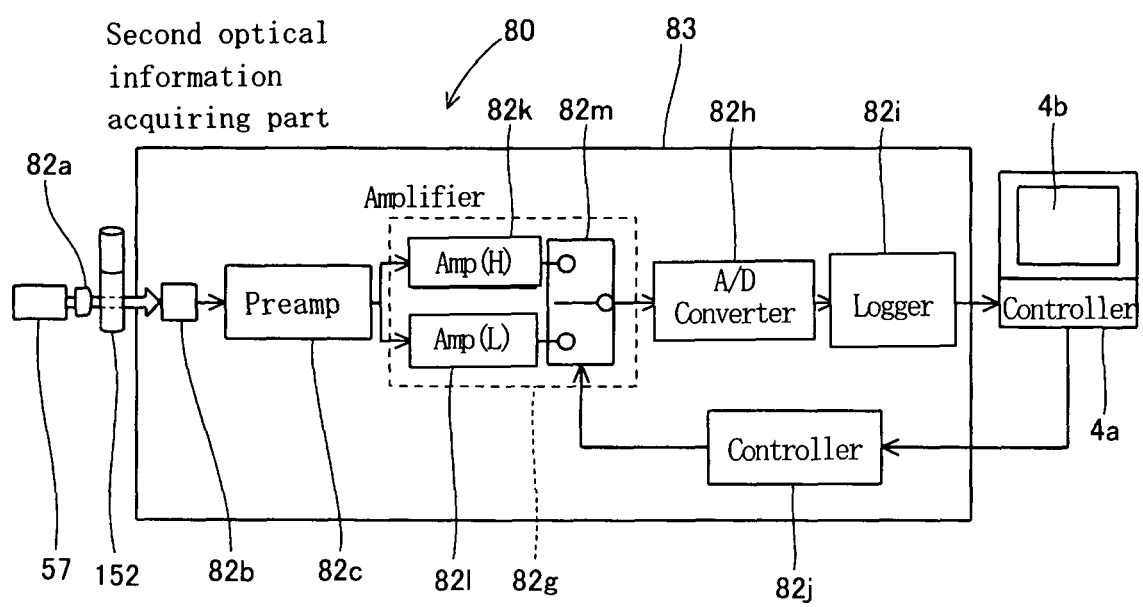
FIG. 15 is a block diagram of a second optical information acquiring section of the embodiment of the sample analyzer shown in FIG. 1.

FIG. 1 is a perspective view showing the general structure of an embodiment of the sample analyzer of the present invention, and FIG. 2 is a plan view of the detection device and transport device of the sample analyzer of the embodiment in FIG. 1. FIG. 3 is a block diagram of the control device of the sample analyzer of the embodiment in FIG. 1. FIGS. 4 through 6 illustrate the structure of a first optical information acquiring section of the embodiment of the sample analyzer shown in FIG. 1. FIGS. 7 through 9 are graphs of the light absorbance spectrums of interference substances. FIGS. 10 through 12 illustrate the structure of a lamp unit of the embodiment of the sample analyzer shown in FIG. 1. FIGS. 13 through 15 illustrate the structure of a second optical information acquiring section of the embodiment of the sample analyzer shown in FIG. 1. The general structure of the sample analyzer 1 which is an embodiment of the present invention is described hereinafter with reference to FIGS. 1 through 15.

The embodiment of the sample analyzer 1 of the present invention is a device for optically measuring and analyzing the amount and degree of activity of specific substances related to blood coagulation and fibrinolysis functions, and blood plasma is used as a sample. The sample analyzer 1 of the present embodiment optically measures a sample (main measurement) using a coagulation time method, synthetic substrate method, and immunoturbidity method. The coagulation time method used in the present embodiment detects and measures the time course of coagulation of a sample as the change in light transmittance. Measurement items include PT (prothrombin time), APTT (active partial thromboplastin time), Fbg (fibrinogen content) and the like. Additionally, ATIII and the like are measurement items of the synthetic substrate method, and D dimer and FDP and the like are measurement items of the immunoturbidity method.

As shown in FIG. 1, the sample analyzer 1 is configured by a detection device 2, transport device 3 disposed on the front side of the detection device 2, and control device 4 electrically connected to the detection device 2.

The control device 4 is configured by a personal computer 401 (PC), and includes a controller 4a, display 4b, and keyboard 4c, as shown in FIG. 1. The controller 4a functions to control the operation of the detection device 2 and transport device 3, and analyze the optical information of the sample acquired by the detection device 2. The controller 4a is configured by a CPU, ROM, RAM and the like. The display 4b is provided to display information related to the interference substances (hemoglobin, bilirubin, chyle (lipids)) present in the sample, and the analysis results obtained by the controller 4a.

The structure of the control device 4 is described below. As shown in FIG. 3, the controller 4a is mainly configured by a CPU 401a, ROM 401b, RAM 401c, hard disk 401d, reading device 401e, I/O interface 401f, communication interface 401g, and image output interface 401h. The CPU 401a, ROM 401b, RAM 401c, hard disk 401d, reading device 401e, I/O interface 401f, communication interface 401g, and image output interface 401h are connected via a bus 401i.

The CPU 401a is capable of executing computer programs stored in the ROM 401b, and computer programs loaded in the RAM 401c. The computer 401 functions as the control device 4 when the CPU 401a executes an application program 404a described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is further used as a work area of the CPU 401 a when these computer programs are being executed.

The hard disk 401d contains various installed computer programs to be executed by the CPU 401 a such as an operating system and application programs and the like, and data used in the execution of these computer programs. Also installed on the hard disk 401d is the application program 404a used to calculate the presence and concentration of interference substances in the present embodiment.

The reading device 401e is configured by a floppy disk drive, CD-ROM drive, DVD-ROM drive or the like, and is capable of reading the computer programs and data stored on a portable recording medium 404. Furthermore, the portable recording medium 404 may also store the application program 404a in the present embodiment; the computer 401 is capable of reading the application program 404a from the portable recording medium 404 and installing the application program 404a on the hard disk 401d.

Not only may the application program 404a be provided by the portable recording medium 404, it also may be provided from an external device connected to the computer 401 so as to be capable of communication over an electric communication line by means of the electric communication line (wire line or wireless). For example, the application program 404a may be stored on the hard disk of a server computer connected to the internet, such that the computer 401 a can access the server computer and download the application program 404a, and then install the application program 404a on the hard disk 401d.

Also installed on the hard disk 401d is an operating system providing a graphical user interface, such as, for example, Windows (registered trademark) of Microsoft Corporation, U.S.A. In the following description, the application program 404a of the present embodiment operates on such an operating system.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f, such that a user can input data in the computer 401 using the keyboard 4c.

The communication interface 401g is, for example, and Ethernet (registered trademark) interface. The computer 401 can send and receive data to and from the detection device 2 using a predetermined communication protocol via the communication interface 401g.

The image output interface 401h is connected to the display 4b configured by an LCD, CRT or the like, such that image signals corresponding to the image data received from the CPU 401a can be output to the display 4b. The display 4b displays an image (screen) in accordance with the input image signals.

The transport device 3 functions to transport a rack 151 containing a plurality of test tubes 150 that accommodate samples to an aspirating position 2a of the detection device 2 (refer to FIG. 2) in order to supply samples to the detection device 2. Furthermore, the transport device 3 has a rack set region 3a that accommodates the racks 151 that hold the test tubes 150 containing unprocessed samples, and a rack receiving region 3b that accommodates the racks 151 that hold test tubes 150 containing processed samples.

The detection device 2 is configured to obtain optical information relating to a supplied samples by optically measuring a samples supplied from the transport device 3. In the present embodiment, optical measurement is performed on a samples dispensed into a cuvette 152 (refer to FIG. 2) of the detection device 2 from a test tube 150 loaded in the rack 151 of the transport device 3. Furthermore, the detection device 2 is provided with a cuvette supplier 10, rotating part 20, sample dispensing arm 30, first optical information acquiring section 40, lamp unit 50, two reagent dispensing arms 60, cuvette transporter 70, second optical information acquiring section 80, rush sample acceptor 90, cuvette disposal 100, and fluid provider 110, as shown in FIGS. 1 and 2.

The cuvette supplier 10 is configured to sequentially supply a plurality of cuvettes 152 (refer to FIGS. 4 and 5) directly inserted by a user to the rotating part 20. As shown in FIG. 2, the cuvette supplier 10 includes a hopper 12 mounted on the device body via a bracket 11 (refer to FIG. 1), two induction plates 13 provided below the hopper 12, support base 14 disposed at the bottom end of the two induction plates 13, and catcher 15 provided at a predetermined distance from the support base 14. The two induction plates 13 are disposed so as to be mutually parallel with a space therebetween so as to be smaller than the diameter of the flange 152a (refer to FIG. 5) of the cuvette 152 and larger than the diameter of the barrel 152b (refer to FIG. 5) of the cuvette 152. The cuvettes 152 supplied into the hopper 12 are configured so as to move smoothly toward the support base 14 with the flange 152a engaged at the top surface of the two induction plates 13. Furthermore, the support base 14 functions to rotate the cuvette 152 that has fallen between the induction plates 13 to a position at which the cuvette 152 can be grabbed by the catcher 15. The catcher 15 is provided to supply the cuvette 152, which has been moved by the support base 14, to the rotating part 20.

The rotating part 20 is provided to transport in a circular direction the cuvettes 152 received from the cuvette supplier 10, and a reagent containers (not shown in the drawings) accommodating reagent to be added to the sample in the cuvette 152. As shown in FIG. 2, the rotating part 20 is configured by a circular reagent table 21, annular reagent table 22 disposed on the outer side of the circular reagent table 21, annular secondary dispensing table 23 disposed on the outer side of the annular reagent table 22, and annular primary dispensing table 24 disposed on the outer side of the annular secondary dispensing table 23. The primary dispensing table 24, secondary dispensing table 23, and reagent tables 21 and 22 are configured so as to be mutually and independently rotatable in both clockwise and counter clockwise directions.

As shown in FIG. 2, the reagent tables 21 and 22 respectively include a plurality of holes 21a and 22a provided at predetermined spacing in the circumferential direction. The holes 21a and 22a of the reagent tables 21 and 22 are provided to load a plurality of reagent containers (not shown in the drawings) that hold various reagents to be added when preparing measurement specimens from samples. Furthermore, the primary dispensing table 24 and secondary dispensing table 23 respectively include a plurality of cylindrical holders 24a and 23a provided at predetermined spacing in the circumferential direction. The holders 24a and 23a are provided to hold the cuvettes 152 received from the cuvette supplier 10. A sample contained in a test tube 150 of the transport device 3 is dispensed to a cuvette 152 held by the holder 24a of the primary dispensing table 24 in a primary dispensing process. Furthermore, a sample contained in the cuvette 152 loaded in the primary dispensing table 24 is dispensed to a cuvette 152 loaded in the holder 23a of the secondary dispensing table 23 in a secondary dispensing process. A pair of holes 24b are formed in the holder 24a at positions corresponding to the mutual sides of the holder 24a, as shown in FIG. 5. The pair of holes 24b are provided for the passage of light emitted from the beam splitter optical fiber 58 of the lamp unit 50 described later.

The sample dispensing arm 30 functions to both aspirate sample contained in a test tube 150 transported to the aspiration position 2a via the transport device 3, and to dispense the aspirated specimen into a cuvette 152 transported to the rotating part 20.

The first optical information acquiring section 40 is configured so as to acquire optical information from a sample in order to measure the presence and concentration of interference substances (hemoglobin, bilirubin, chyle) in the sample before adding reagent. Specifically, the presence and concentrations of interference substances are measured using four types of light (405 nm, 575 nm, 660 nm, 800 nm) among five types of light (340 nm, 405 nm, 575 nm, 660 nm, 800 nm) emitted from the lamp unit 50 described later. The 405 nm wavelength light is absorbed by chyle, hemoglobin, and bilirubin, as shown in FIGS. 7 through 9. That is, chyle, hemoglobin, and bilirubin influence the optical information measured using light at a wavelength of 405 nm. Furthermore, light at a wavelength of 575 nm is absorbed by chyle and hemoglobin, although essentially is not absorbed by bilirubin. That is, chyle and hemoglobin influence the optical information measured using light at a wavelength of 575 nm. Light at wavelengths of 660 nm and 800 nm are absorbed by chyle, although essentially are not absorbed by bilirubin and hemoglobin. That is, chyle influences the optical information measured using light at wavelengths of 660 nm and 800 nm. As shown in FIG. 9, chyle absorbs light from the low wavelength region 405 nm to the high wavelength region 800 nm, with chyle absorbing more light at the 660 nm wavelength than at the 800 nm wavelength. That is, the optical information measured using light at the 800 nm wavelength is less influenced by chyle than optical information at the 660 nm wavelength.

The acquisition of sample optical information by the first optical information acquiring section 40 occurs before optically measuring (main measurement) the sample by the second optical information acquiring section 80. As shown in FIGS. 2 and 4, the first optical information acquiring section 40 acquires optical information from the sample within the cuvette 152 held by the holder 24a of the primary dispensing table 24. The first optical information acquiring section 40 includes an emission side holder 41 on the light emitting side, photoelectric conversion element 42 (refer to FIG. 5), receiving side holder 43 on the light receiving side, bracket 44, and base plate 45 for installing the photoelectric conversion element 42, as shown in FIGS. 4 and 5.

The receiving side holder 43 is formed so as to accept the base plate 45 in which the photoelectric conversion element 42 is installed, and is mounted on the emission side holder 41 via the bracket 44 (refer to FIG. 4), as shown in FIG. 5. A cover 43a, which is provided with a slit 43b at a predetermined position, is mounted on the receiving side holder 43. The light from the beam splitter optical fiber 58 (described later) that has passed through the cuvette 152 held by the holder 24a of the primary dispensing table 24 is detected by the photoelectric conversion element 42 through the slit 43b of the receiving side holder 43, and the pair of holes 24b of the holder 24a.

The base plate 45 functions to amplify the electrical signals detected by the photoelectric conversion element 42, and transmit the electrical signals to the controller 4a of the control device 4. The base plate 45 is configured by a pre amp 45a, amplifier 45b, A/D converter 45c, and controller 45d. The amplifier 45b has an amp 45e, and electronic volume 45f. The pre amp 45a and amp 45e are provided to amplify the electrical signals detected by the photoelectric conversion element 42. The amp 45e of the amplifier 45b is configured so as to regulate the gain (amplification factor) of the amp 45e by inputting a control signal from the controller 45d to the electronic volume 45f. The A/D converter 45c is provided to convert the electrical signals (analog signals) amplified by the amp 45e to digital signals.

The controller 45d is configured so as to change the gain (amplification factor) of the amp 45e to match the periodic change in the wavelength (340 nm, 405 nm, 575 nm, 660 nm, 800 nm) of the light emitted from the beam splitter optical fiber 58 of the lamp unit 50 which is described later. Furthermore, as shown in FIG. 6, the controller 45d is electrically connected to the controller 4a of the control device 4, and sends the digital signal data (optical information) acquired by the first optical information acquiring section 40 to the controller 4a of the control device 4. Thus, in the control device 4 the light absorbance of the sample within the cuvette 152 is determined relative to the five kinds of light emitted from the beam splitter optical fiber 58, and the presence and concentrations of interference substances in the sample are analyzed by performing data analysis of the digital signal data from the first optical information acquiring section 40. In the present embodiment, a determination is made as to whether or not to analyze optical information acquired by the second optical information acquiring section 80 based on the presence and concentrations of interference substances in the sample.

In the present embodiment, the lamp unit 50 is provided to supply light to be used in the optical measurements performed by the first optical information acquiring section 40 and second optical information acquiring section 80, as shown in FIG. 2. That is, a single lamp unit 50 is configured so as to be used commonly by the first optical information acquiring section 40 and second optical information acquiring section 80. As shown in FIGS. 10 and 11, the lamp unit 50 is configured by a halogen lamp 51 as a light source, collective lenses 52a through 52c, disk-shaped filter 53, motor 54, transmission light sensor 55, optical fiber coupler 56, eleven beam splitter optical fibers 57 (refer to FIG. 11), and a single beam splitter optical fiber 58 (refer to FIG. 11).

As shown in FIG. 10, the halogen lamp 51 is accommodated in a lamp case 51a having a plurality of fins to dissipate the heat generated by the halogen lamp 51 via air cooling.

The collective lenses 52a through 52c function to collect the light emitted from the halogen lamp 51. The collective lenses 52a through 52c are disposed on the optical path to guide the light emitted from the halogen lamp 51 to the optical fiber coupler 56. Furthermore, the light emitted from the halogen lamp 51 and collected by the collective lenses 52a through 52c is transmitted through one filter among the optical filters 53b through 53f of the filter part 53, which is described later.

Furthermore, the filter part 53 of the lamp unit 50 is mounted on the motor shaft (not shown in the drawing) of the motor 54 so as to be rotatable, as shown in FIG. 12. The filter part 53 is provided with a filter plate 53a with five optical filters 53b through 53f that have respectively different light transmitting characteristics (transmission wavelengths). The filter plate 53a is provided with five holes 53g for mounting the optical filters 53b through 53f, and a hole 53h that can be blocked so as to not transmit light. The five holes 53g are respectively provided with five optical filters 53b, 53c, 53d, 53e, and 53f having respectively different light transmission characteristics (transmission wavelengths). The holes 53g and 53h are provided at predetermined angular intervals (equal spacing of 60 degrees in the present embodiment) in the direction of rotation of the filter part 53. The hole 53h is a reserve hole for installing an addition filter when necessary.

The optical filters 53b, 53c, 53d, 53e, and 53f transmit light at wavelengths of 340 nm, 405 nm, 575 nm, 660 nm, and 800 nm, respectively, and do not transmit light of different wavelength. Therefore, the optical filters 53b, 53c, 53d, 53e, and 53f have wavelength characteristics so as to transmit light at 340 nm, 405 nm, 575 nm, 660 nm, and 800 nm, respectively.

Furthermore, the filter plate 53a is provided with six slits at predetermined angular intervals (60 degree intervals in the present embodiment) in the circumferential direction. One of these six slits is the origin point slit 53j that has a wider width in the rotation direction of the filter plate 53a than the other five normal slits 53i. The origin point slit 53j and normal slits 53i are formed at predetermined angular intervals (equal intervals of sixty degrees in the present embodiment) at intermediate angular positions between adjacent holes 53g and 53h.

In the present embodiment, the filter part 53 is configured to rotate continuously when light is emitted from the lamp unit 50 to the cuvette 152 on the primary dispensing table 24. Therefore, the five optical filters 53b through 53f having different light transmitting characteristics and the single blocked hole 53h (refer to FIG. 6) are sequentially arranged on the optical path of the light collected by the collective lenses 52a through 52c (refer to FIG. 5) in conjunction with the rotation of the filter plate 53a. Therefore, light of five different wavelengths are sequentially emitted.

The transmission light sensor 55 is provided to detect the passage of light through the origin point slit 53j and normal slits 53i in conjunction with the rotation of the filter part 53, as shown in FIG. 12. The sensor 55 detects light from the light source through the slit via the light receiving unit as it passes through the origin point slit 53j and normal slits 53i, and outputs a detection signal. The detection signal output by the sensor 55 has a longer output time when light passes through the origin point slit 53j than the output signal when light passes through the normal slits 53i since the origin point slit 53j has a larger width than the normal slits 53i. Therefore, the filter part 53 can be monitored for normal rotation based on the detection signals from the sensor 55.

The optical fiber coupler 56 functions to direct the light that has passed through the optical filters 53b through 53f to the respective eleven beam splitter fibers 57 and the single beam splitter optical fiber 58. That is, in the present embodiment the optical fiber coupler 56 simultaneously guides light of like quality to the eleven beam splitter optical fibers 57 and the single beam splitter optical fiber 58. Furthermore, the leading ends of the eleven beam splitter optical fibers 57 are connected to the second optical information acquiring section 80, and light from the lamp unit 50 is directed to the measurement specimen within a cuvette 152 set in the second optical information acquiring section 80, as shown in FIG. 2. Specifically, the eleven beam splitter optical fibers 57 are disposed so as to supply light to ten insertion holes 81a and one reference light measurement hole 81b which are parts of the second optical information acquiring section 80 described later, as shown in FIG. 13. Unlike the eleven beam splitter optical fiber 57, the leading end of the single beam splitter optical fiber 58 is connected to the first optical information acquiring section 40, and directs light from the lamp unit 50 to the sample within the cuvette 152 held by the holder 24a of the primary dispensing table 24, as shown in FIGS. 2 and 4. Therefore, five kinds of light having different wavelength characteristics consecutively passes through the optical filters 53b through 53f, and is supplied to the first optical information acquiring section 40 and second optical information acquiring section 80 via the beam splitter optical fibers 57 and 58.

As shown in FIGS. 1 and 2, the reagent dispensing arm 60 is provided to mix reagent with the sample in the cuvette 152 by dispensing the reagent within a reagent container (not shown in the drawings) loaded on the rotating part 20 into a cuvette 152 held in the rotating part 20. In this way a measurement specimen is prepared by adding reagent to a sample after the sample has been optically measured by the first optical information acquiring section 40. The cuvette transporter 70 is provided to move the cuvette 152 between the rotating part 20 and the second optical information acquiring section 80.

The second optical information acquiring section 80 functions to heat the measurement specimen prepared by adding reagent to a sample, and measure optical information from the measurement specimen. As shown in FIG. 2, the second optical information acquiring section 80 is configured by a cuvette loader 81, and detection unit 82 disposed below the cuvette loader 81. The cuvette loader 81 is provided with ten insertion holes 81a for inserting cuvettes 152 (refer to FIG. 2), and a single reference light measurement hole 81b for measuring a reference light and in which a cuvette is not inserted. The cuvette loader 81 has a built-in heater (not shown in the drawing) for heating a cuvette 152 loaded in the insertion holes 81a to a predetermined temperature.

In the present embodiment the reference light measurement hole 81b is provided for monitoring the characteristics of the light emitted from the beam splitter optical fiber 57. The cuvette transporter 70 is controlled so as to not load a cuvette 152 in the reference light measurement hole 81b. In this way the characteristics (ex. fluctuation) of the light inherent to the lamp can be monitored to the exclusion of the optical information caused by the cuvette 152 and the measurement specimen within the cuvette 152. Specifically, characteristics such as fluctuation and the like originating in the halogen lamp 51 of the lamp unit 50 (refer to FIG. 10) are detected as electrical signals by directly receiving the light emitted by the beam splitting optical fibers 57 via a reference light photoelectric conversion element 82e of the detection unit 82. Signals corresponding to the transmission light of the measurement specimen are corrected by a subtracting the characteristics of the detected light from the signals corresponding to the transmission light of the measurement specimen within the cuvette 152 inserted in the insertion hole 81a. Thus, it is possible to suppress minute differences caused by the characteristics of the light in each photometric measurement.

The detection part 82 of the second optical information acquiring section 80 is configured so as to be capable of performing optical measurement (main measurement) under a plurality of conditions on measurement specimen within a cuvette 152 inserted in the insertion hole 81a. As shown in FIGS. 8 and 9, the detection part 82 is provided with a collimator lens 82a, photoelectric conversion element 82b, and preamp 82c corresponding to each insertion hole 81a in which a cuvette 152 is inserted, and a reference light collimator lens 82d, reference light photoelectric conversion element 82e, and reference light preamp 82f corresponding to the reference light measurement hole 81b (refer to FIG. 1).

As shown in FIGS. 13 and 14, the collimator lens 82a is disposed between the end of the beam splitter optical fiber 57 that guides the light emitted from the lamp unit 50 (refer to FIG. 10), and the corresponding insertion hole 81a. The collimator lens 81a is provided to render the light beams emitted from the beam splitter optical fiber 57 in parallel rays. The photoelectric conversion element 82b mounted on the surface on the insertion hole 81a side of the base plate 83 so as to face the end of the beam splitter optical fiber 57 with the insertion hole 81 a therebetween. The photoelectric conversion element 82b functions to detect the light transmitted through the measurement specimen (hereafter referred to as "transmission light") when light irradiates the measurement specimen within the cuvette 152 inserted in the insertion hole 81a, and outputs electric signals (analog signals) corresponding to the detected transmission light. The photoelectric conversion element 82b is disposed so as to receive five kinds of light emitted from the beam splitter optical fiber 57 of the lamp unit 50. The 660 nm wavelength light emitted from the beam splitter optical fiber 57 is the main wavelength used when measuring Fbg (fibrinogen content), PT (prothrombin time), and APTT (active partial thromboplastin time). The 800 nm wavelength light is a sub wavelength used when measuring Fbg, PT, and APTT. The 405 nm wavelength is used for measuring ATIII, which is a measurement item in the synthetic substrate method, and 800 nm wavelength light is used to measure D dimer and FDP, which are measurement items in the immunoturbidity method. The wavelength for measuring platelet coagulation is 575 nm. Thus, the sample analyzer 1 of the present embodiment obtains light of a plurality of wavelengths passing through the optical filters 53b through 53f of the filter part 53 emitted from the halogen lamp 51 of a single light source, and measures various items using this light.

The preamp 82c is mounted on the opposite surface of the base plate 83 relative to the insertion hole 81a so as to amplify the electric signal (analog signal) output from the photoelectric conversion element 82b.

As shown in FIG. 15, the base plate 83 is provided with the photoelectric conversion elements 82b (reference light photoelectric conversion element 82e), preamps 82c (reference light preamp 82f), as well as amplifier part 82g, A/D converter 82h, logger 82i, and controller 82j. The amplifier 82g includes amp (L) 82k with a predetermined gain (amplification factor), amp (H) 82l with a gain (amplification factor) higher than the amp (L) 82k, and switch 82m. In the present embodiment, electrical signals from the preamp 82c are input to both the amp (L) 82k and the amp (H) 82l. The amp (L) 82k and amp (H) 82l are provided to further amplify the electric signals from the preamps 82c. The switch 82m is provided to selectively either output the electric signals from the amp (L) 82k to the A/D converter 82h, or output the electric signal from the amp (H) 82l to the A/D converter 82h. The switch 82m is configured so as to perform a switching operation via the input of control signals from the controller 82j.

The A/D converter 82h is provided to convert the electric signals (analog signals) from the amplifier part 82g to digital signals. The logger 82i functions to temporarily save the digital signal data (photometric information) from the A/D converter 82h. The logger 82i is electrically connected to the controller 4a of the control device 4, and sends the digital data obtained by the second optical information acquiring section 80 to the controller 4a of the control device 4. Thus, in the control device 4 the digital signal data (optical information) received from the second optical information section 80 are analyzed based on the analysis result of the digital signal data (optical information) previously acquired by the first optical information acquiring section 40, and the data are displayed on the display 4b.

As shown in FIGS. 1 and 2, the rush sample acceptor 90 is provided to perform a sample analysis process on sample requiring immediate processing. The rush sample acceptor 90 is capable of performing an interrupt on behalf of a rush sample when there is an on-going sample analysis process being performed on a sample supplied from the transport device 3. The cuvette disposal 100 is provided to dispose of cuvettes from the rotating part 20. As shown in FIG. 2, the cuvette disposal 100 is configured by a cuvette waste part 101, disposal hole 102 provided at predetermined spacing from the cuvette waste part 101 (refer to FIG. 1), and waste box 103 provided below the disposal hole 102. The cuvette waste part 101 is provided to move a cuvette 152 from the rotating part 20 to the waste box 103 via the disposal hole 102 (refer to FIG. 1). A fluid provider 110 is provided to supply a fluid such as cleaning liquid to a nozzle provided on each dispensing arm during the shutdown process of the sample analyzer 1.

Figure 16:
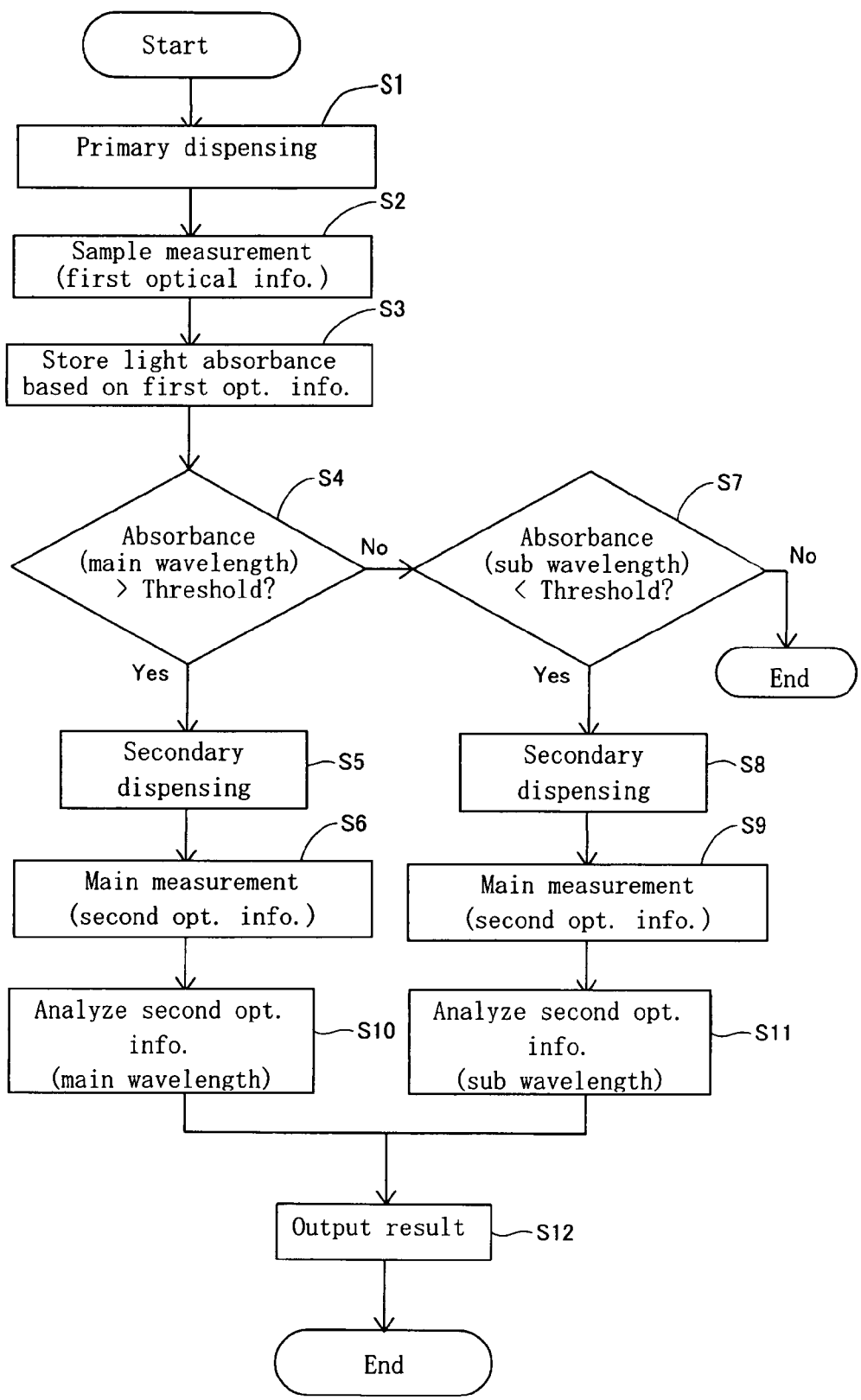
FIG. 16 is a flow chart showing the sequence of the sample analyzing operation of the embodiment of the sample analyzer shown in FIG. 1.

FIG. 16 is a flow chart showing the sequence of the sample analyzing operation of the embodiment of the sample analyzer shown in FIG. 1. The sample analysis operation of the sample analyzer 1 is described in detail below with reference to FIGS. 1 through 6, 10, 12, 14, and 16. The operation of measurements using the coagulation time method is described below.

The sample analyzer 1 is first initialized by turning ON the power supplies of the detection device 2 and control device 4 of the sample analyzer 1 shown in FIG. 1. In this way, an operation is performed to return each dispensing arm and the mechanism that moves the cuvettes 152 to the initial positions, and software stored in the controller 4a of the control device 4 is initialized.

Then, the rack 151 loaded with test tubes 150 containing samples is transported by the transport device shown in FIG. 2. Thus, the rack 151 is transported from the rack set region 3a to a position corresponding to the aspirating position 2a of the detection device 2.

In step S1, a predetermined amount of sample is aspirated from the test tube 150 via the sample dispensing arm 30. The sample dispensing arm 30 is then moved above the cuvette 152 held on the primary dispensing table 24 of the rotating part 20. Thereafter, the sample within the cuvette 152 is allocated by discharging the sample from the sample dispensing arm 30 into the cuvette 152 of the primary dispensing table 24.

Then, the primary dispensing table 24 is rotated to move the cuvette 152 containing the dispensed sample to a position at which the sample can be measured by the first optical information acquiring section 40. Thus, in step S2, the sample is optically measured by the first optical information acquiring section 40, and optical information is acquired from the sample. Specifically, five kinds of light (340 nm, 405 nm, 575 nm, 660 nm, 800 nm) passes through the sample within the cuvette 152 held by the holder 24a of the primary dispensing table 24 (refer to FIG. 5), and is sequentially detected by the photoelectric conversion element 42. Then, the electrical signals detected by the photoelectric conversion element 42 are amplified by the preamp 45a (refer to FIG. 6) and amp 45e, and converted to digital signals by the A/D converter 45c. Thereafter, the digital signals are sent by the controller 45d to the controller 4a of the control device 4. Thus, the acquisition of optical information (first optical information) from a sample by the first optical information acquiring section 40 is completed.

In step S3, the controller 4a of the control device 4 calculates the sample light absorbance using the received digital signal data (first optical information), then calculates the presence and concentrations of interference substances (hemoglobin, bilirubin, chyle) in the sample. Specifically, the controller 4a of the control device 4 calculates the sample light absorbance based on the optical information (first optical information) acquired using four kinds of light (405 nm, 575 nm, 660 nm, 800 nm) emitted from the lamp unit 50 (refer to FIG. 10), and stores the calculated light absorbance in the RAM 401c.

Thereafter, in step S4, a determination is made as to whether or not the light absorbance at the main wavelength is less than a threshold value among the light absorbances stored in the RAM 401c. Specifically, when the sample measurement item is an item using the coagulation time method such as PT, APTT, Fbg or the like, a determination is made as to whether or not the light absorbance calculated from the first optical information measured using light of 660 nm wavelength is less than a threshold value (for example, 2.0). The wavelength of 660 nm is the main wavelength for the measurement of the above mentioned measurement items.

When the main wavelength light absorbance calculated from the first optical information measured by the first optical information acquiring section 40 is below the threshold value in step S4, then in step S5 a predetermined amount of sample is aspirated from the cuvette 152 held by the holder 24a on the primary dispensing table 24. Thereafter, the secondary dispensing process is performed by discharging predetermined amounts of sample from the dispensing arm 30 to a plurality of cuvettes 152 on the secondary dispensing table 23. Then, the reagent dispensing arm 60 is actuated and reagent within the reagent container (not shown in the drawing) loaded in the reagent table 21 and 22 is added to the sample within the cuvette 152 on the secondary dispensing table 23. Thus, a measurement specimen is prepared. The cuvette 152 containing the measurement specimen on the secondary dispensing table 23 is then moved to the insertion hole 81a of the cuvette loader 81 of the second optical information acquiring section 80.

In step S6, a plurality (ten types) of optical information (second optical information) are acquired when the detection unit 82 of the second optical information acquiring section 80 optically measures (main measurement) the measurement specimen within the cuvette 152 under a plurality of conditions. Specifically, the cuvette 152 inserted in the insertion hole 81a of the cuvette loader 81 is first heated to a predetermined temperature by a heating device (not shown in the drawing). Thereafter, the cuvette 152 in the cuvette loader 81 is illuminated by light from the beam splitter optical fiber 57 of the lamp unit 50, as shown in FIG. 14. Light of five different wavelengths (340 nm, 405 nm, 575 nm, 660 nm, 800 nm) emitted from the beam splitter optical fiber 57 periodically illuminates via the rotation of the filter part 53 (refer to FIG. 12). The light of each wavelength emitted from the beam splitter optical fiber 57 passes through the cuvette 152 and the measurement specimen within the cuvette 152 and is sequentially detected by the photoelectric conversion element 82b. The electrical signals corresponding to the light of five difference wavelengths converted by the photoelectric conversion element 82b are amplified by the pre amp 82c, and subsequently input to the amplifier 82g.

In the amplifier 82g, the electrical signals corresponding to the light of five different wavelengths from the preamp 82c (refer to FIG. 15) are each input to the amp (H) 82l having the high amplification factor and the amp (L) 82k having the normal amplification factor. The controller 82j controls the switch 82m so as to output the electric signals that have been amplified by the amp (H) 82l are output to the A/D converter 82h, and thereafter the electric signals that have been amplified by the amp (L) 82k are output to the A/D converter 82h. The switch 82m repeatedly switches in accordance with the timing of the rotation of the filter part 53 (refer to FIG. 12) in the lamp unit 50. Thus, the electrical signals corresponding to the light at five different wavelengths are respectively amplified by two different amplification factors in the amplifier part 82g, and a total of ten electrical signals are repeatedly output to the A/D converter 82h. These ten electric signals are converted to digital signals by the A/D converter 82h and the digital signals are temporarily stored in the logger 82i, and subsequently these digital signals are sequentially transmitted to the controller 4a of the control device 4. Thus, the acquisition of a plurality (ten types) of optical information (second optical information) for a measurement specimen is completed by the second optical information acquiring section 80.

When the main wavelength light absorbance calculated from the first optical information measured by the first optical information acquiring section 40 exceeds the threshold value in step S4, then in step S7 a determination is made as to whether or not the light absorbance at the sub wavelength calculated from the first optical information measured by the first optical information acquiring section 40 is less than a threshold value. Specifically, when the sample measurement item is an item using the coagulation time method such as PT, APTT, Fbg or the like, a determination is made as to whether or not the light absorbance calculated from the first optical information measured using light of 800 nm wavelength is less than a threshold value (for example, 2.0). The wavelength of 800 nm is the sub wavelength for measurement of the above mentioned measurement items.

When the light absorbance at the sub wavelength calculated from the first optical information measured by the first optical information acquiring section 40 is below the threshold value in step S7, then in steps S8 and S9 a plurality (ten kinds) of optical information (second optical information) are acquired from the measurement specimen by the second optical information acquiring section 80 similar to steps S5 and S6.

However, when the light absorbance at the sub wavelength calculated from the first optical information measured by the first optical information acquiring section 40 exceeds the threshold value in step S7, it is determined that it will be difficult to analyze the data with acceptable reliability due to the large influence of interference substances (bilirubin, hemoglobin, chyle) contained in the sample, and the main measurement is terminated. Thus, wasteful use of reagent is prevented since a measurement specimen is not prepared by adding reagent to a sample that can not be analyzed due to the excessive influence of interference substances. In the case of difficulty in performing measurement with high reliability (when the main measurement is terminated), the light passing through the specimen may be blocked due to the presence of large amounts of interference substance in the sample detected by the first optical information acquiring section 40 such that the transmission light that has passed through the sample can not be effectively detected.

After the acquisition of the second optical information (main measurement) by the second optical information acquiring section 80 in step S6, the second optical information of the measurement specimen measured at the main wavelength is sent to the controller 4a of the control device 4 from among the plurality of second optical information measured by the second optical information acquiring section 80, and this optical information is analyzed in step S10 via the application program 404a installed on the hard disk 401d of the controller 4a. Specifically, when the sample measurement item is PT, the second optical information measured using the light of wavelength 660 nm (the main wavelength for PT) is sent to the controller 4a of the control device 4. Thereafter, the controller 4a, which has received the second optical information acquired at the main wavelength, outputs the analysis result based on this second optical information.

Similarly, after the acquisition of the second optical information (main measurement) by the second optical information acquiring section 80 in step S9, the second optical information of the measurement specimen measured at the sub wavelength is sent to the controller 4a of the control device 4 from among the plurality of second optical information measured by the second optical information acquiring section 80, and this optical information is analyzed in step S11 via the application program 404a installed on the hard disk 401d of the controller 4a. Specifically, when the sample measurement item is PT, the second optical information measured using the light of wavelength 800 nm (the sub wavelength for PT) is sent to the controller 4a of the control device 4. Thereafter, the controller 4a, which has received the second optical information acquired at the sub wavelength, outputs the analysis result based on this second optical information.

After the analysis is completed by the controller 4a of the control device 4 in steps S10 and S11, the analysis results obtained in steps S10 and S11 are displayed on the display 4b in step S12. Thus, the sample analysis operation of the sample analyzer 1 is completed.

In the present embodiment, light can be supplied to both the sample if the first optical information acquiring section 40 and the measurement specimen of the second optical information acquiring section 80 by providing the lamp unit 50 that commonly supplies light for illuminating the sample in the first optical information acquiring section 40 and light for illuminating the measurement specimen in the second optical information acquiring section 80 as described above. Thus, the sample analyzer 1 is rendered more compact because the lamp unit 50 is commonly used to supply light to the sample of the first optical information acquiring section 40 and to the measurement specimen of the second optical information acquiring section 80.

In the present embodiment, light of substantially identical quality can be supplied to both the sample if the first optical information acquiring section 40 and the measurement specimen of the second optical information acquiring section 80 by providing the lamp unit 50 that commonly supplies light for illuminating the sample in the first optical information acquiring section 40 and light for illuminating the measurement specimen in the second optical information acquiring section 80. Thus, the estimation as to whether or not accurate measurement by the second optical information acquiring section 80 is possible is accurately accomplished based on the results of the measurement by the first optical information acquiring section 40 using light of identical quality. Analysis of samples that are not analyzable can be prevented if the second optical information used for analysis is selected from among a plurality of second optical information based on the first optical information acquired from the sample. As a result, a greater number of samples can be analyzed.

In the present embodiment, light of substantially identical quality emitted from the halogen lamp 51 can be readily directed to both the first optical information acquiring section 40 and second optical information acquiring section 80 by providing the halogen lamp 51, the single beam splitter optical fiber 58 for guiding light emitted from the halogen lamp 51 to the sample of the first optical information acquiring section 40, and the eleven beam splitter optical fibers 57 for guiding light emitted from the halogen lamp 51 to the measurement specimen in the second optical information acquiring section 80. Furthermore, in the present embodiment, the lamp unit 50 includes collective lenses 52a through 52c for guiding the light emitted from the halogen lamp 51 to the beam splitter optical fiber 58 and beam splitter optical fibers 57. According to this configuration, light emitted from a single lamp can be directed to the beam splitter optical fiber 58 and beam splitter optical fiber 57. In the present embodiment, the second optical information acquiring section 80 includes a plurality of insertion holes 81a for loading cuvettes containing measurement specimens, and the beam splitter optical fiber 57 has a plurality of branches and these plurality of branches direct light to the plurality of insertion holes 81a respectively. According to this configuration, light illuminates the measurement specimens in the plurality of cuvettes loaded in the plurality of insertion holes 81a. As a result, a plurality of measurement specimens prepared by adding reagent to a sample can be measured at once.

In the present embodiment, light of a plurality of wavelengths is supplied to the first optical information acquiring section 40 and second optical information acquiring section 80 by providing the lamp unit 50 with the filter part 53 which has optical filter 52b through 53f with five different light transmission characteristics (transmission wavelengths). Thus, a plurality of first optical information can be acquired by illuminating the sample in the first optical information acquiring section 40 with light of a plurality of wavelengths, and a plurality of second optical information can be acquired by illuminating the measurement specimen in the second optical information acquiring section 80 with light of a plurality of wavelengths. As a result, the measurement specimen can be measured at an appropriate wavelength even when the appropriate wavelength for measuring the measurement specimen differs according to the type of reagent added to the sample and the item being measured (PT (prothrombin time), APTT (active partial thromboplastin time), Fbg (fibrinogen content), ATIII, D dimer, FDP, platelet coagulation and the like).

The sample analyzer 1 of the present embodiment is further provided with a controller 4a for selecting the second optical information acquired at a wavelength suitable for analysis based on the first optical information of a sample acquired using light of a plurality of wavelengths. According to this configuration, when the second optical information measured using light of a predetermined wavelength is unsuitable for a measurement item, the second optical information least influenced by interference substances can be analyzed without analysis error if second optical information is selected that was measured using light of the high wavelength that is least affected by in the interference substance. As a result, more sample can be analyzed. Specifically, when the sample is being analyzed for a measurement item that uses the coagulation time method such as PT, APTT, Fbg and the like and the light absorbance of the sample acquired using 660 nm wavelength (main wavelength) light exceeds a threshold value (for example, 2.0), and when the light absorbance of a sample acquired using 800 nm wavelength (sub wavelength) light is less than the threshold value (for example, 2.0), second optical information acquired using the 800 nm wavelength that is essentially unaffected by interference substances (hemoglobin, bilirubin) can be analyzed by analyzing the second optical information of the measurement specimen acquired using the 800 nm wavelength (sub wavelength) light in step S11. As a result, it is possible to prevent analysis errors caused by the presence of interference substances in a sample when analyzing second optical information.

In the present embodiment, the controller 4a controls whether or not a measurement specimen is prepared based on the first optical information of a sample acquired using light of a plurality of wavelengths. Specifically, wasteful use of reagent can be prevented since reagent is not added to a sample that can not be analyzed with acceptable reliability by terminating the measurement when the sample light absorbance acquired using 660 nm wavelength (main wavelength) light exceeds a threshold (for example, 2.0) and the sample light absorbance acquired using 800 nm wavelength (sub wavelength) light exceeds a threshold (for example, 2.0). Moreover, analysis efficiency is improved since second optical information is not acquired from samples from which highly reliable results can not be obtained.

The embodiment of the present disclosure is offered as an example in all respects and should not be construed limiting in any way. The scope of the present invention is defined by the scope of the claims and not be the description of the embodiment, and includes all modifications within the scope of the claims and the meanings and equivalences therein.

For example, in the example of the present embodiment, ten types of optical information (digital signal data) are acquired from the second optical information acquiring section 80 using a lamp unit that emits light of five different wavelengths, and the second optical information determined to be best suited for analysis is selected from these ten types of acquired second optical information and analyzed. However, the present invention is not limited to this configuration. For example, measurement conditions may be selected according to the analysis result of the first optical information acquired by the first optical information acquiring section 40, and second optical information can be acquired under the selected conditions.

In the present embodiment, a halogen lamp is used as the light source for supplying light of a plurality of wavelengths to the first optical information acquiring section 40 and second optical information acquiring section 80. However, the present invention is not limited to this configuration. For example, an HID lamp, LED or the like may also be used. The light source may also be a light source that emits light including a plurality of wavelengths such as white light, or a single light source that includes a plurality of light sources that each emits light of a different wavelength.

In the present embodiment, light of five different wavelengths are emitted by rotating a filter plate provided with five optical filters that transmit light of different wavelengths, and having this light emitted from the lamp unit pass through each of the optical filters. However, the present invention is not limited to this configuration. For example, light of a plurality of wavelengths may be emitted by providing a plurality (for example, five) LEDs that emit light of respectively different wavelengths such that the LEDs sequentially or simultaneously emit light. Moreover, light including a mixture of a plurality of wavelengths such as white light may be emitted to illuminate cuvettes without emitting separate light of a plurality of wavelengths, so as to have the light that passes through the cuvettes pass through a plurality of optical filters and cause the light of difference wavelengths to be received by light receiving elements.

In the present embodiment, a structure is used to dispense reagent via a dispensing arm 60 to a cuvette containing a predetermined amount of sample in order to prepare a measurement specimen by adding reagent to the sample. However, the present invention is not limited to this configuration insofar as reagent is ultimately mixed with a sample. For example, a predetermined amount of sample may be dispensed to a container that already contains a predetermined amount of reagent. Moreover, a structure for moving a predetermined amount of a fluid, that is, sample or reagent, may be provided without aspirating reagent from a reagent container, moving to the position of a cuvette containing a sample, and discharging the aspirated reagent to the cuvette as in the case of the dispensing arm of the present embodiment. For example, one end of a tube may be connected to a reagent container and a container accommodating a sample may be moved near the other end of the tube so as to supply reagent from the other end of the tube to the container accommodating the sample.

Although the present embodiment has been described by way of example of optically measuring (main measurement) a sample (measurement specimen) using coagulation time, the present invention is not limited to this arrangement inasmuch as optical measurement of a sample (measurement specimen) may also be accomplished using a method other than coagulation time, such as the synthetic substrate method, immunoturbidity method and the like. The present invention is not limited to measurement items related to coagulation and fibrinolysis of blood, inasmuch as the present invention is generally applicable to clinical measurement items in which interference substances in a sample are problematic.

Although the present embodiment has been described by way of example of providing a detection device and control device separately, the invention is not limited to this configuration inasmuch as the control device functions may be provided in the detection device.

What is claimed is:

1. A sample analyzer comprising:
    an annular table for transporting a sample container accommodating a sample;
    a light source section for emitting light;
    a first optical information acquiring section for illuminating the sample in the sample container on the annular table with the light emitted by the light source section, and for acquiring first optical information; and
    a second optical information acquiring section for illuminating a measurement specimen prepared by adding a reagent to the sample with light emitted by the light source section, and for acquiring second optical information, wherein the second optical information acquiring section is so configured that a measurement specimen container accommodating the measurement specimen is set thereon;
    wherein the light source section comprises;
    a light source;
    a first light guide for guiding light emitted from the light source to the sample in the first optical information acquiring section; and
    a second light guide for guiding light emitted from the light source to the measurement specimen in the second optical information acquiring section; and
    wherein
    the second optical information acquiring section has a plurality of container holding sections for holding specimen containers that accommodate measurement specimens;
    the second light guide has a plurality of branches;
    the branches are connected to the container holding sections; and
    light is supplied from the light source to the plurality of container holding sections.

2. The sample analyzer of claim 1, wherein the light source section has an emission wavelength switching part, and the light source section sequentially emits light of different wavelengths.

3. The sample analyzer of claim 2, wherein:
    the first optical information acquiring section acquires first optical information, of a sample, corresponding to each wavelength using the light of different wavelengths sequentially emitted from the light source section;
    the second optical information acquiring section acquires second optical information, from a measurement specimen, corresponding to each wavelength using the light of different wavelengths sequentially emitted from the light source section; and
    the sample analyzer further comprises a control section for selecting second optical information for analysis from among the second optical information, based on the first optical information.

4. The sample analyzer of claim 3, further comprising:
    a reagent adding section for preparing a measurement specimen by adding reagent to a sample, and
    the reagent adding section adding reagent to a sample on the basis of the first optical information.

5. The sample analyzer of claim 4, wherein the reagent adding section refrains from adding reagent to the sample when the first optical information meets a predetermined condition.

6. The sample analyzer of claim 3, wherein:
    the emission wavelength switching part switches the wavelength of the light emitted from the light source section to emit light of a first wavelength and light of a second wavelength;

the control section determines whether the first optical information of the sample acquired using light of the first wavelength is within a first range; and the control section analyzes the second optical information of the measurement specimen acquired using light of the first wavelength when the first optical information of the sample acquired using the light of the first wavelength is within the first range.

7. The sample analyzer of claim 6, wherein:

the control section determines whether or not first optical information of the sample acquired using light of the second wavelength meets a predetermined condition when first optical information of the sample acquired using light of the first wavelength is outside the first range; and the control section analyzes second optical information of the measurement specimen acquired using light of the second wavelength when first optical information of the sample acquired using light of the second wavelength meets the predetermined condition.

8. The sample analyzer of claim 3, wherein the light source is a light emitting element for emitting light having a plurality of wavelengths.

9. The sample analyzer of claim 8, wherein:

the emission wavelength switching part comprises a first optical filter and a second optical filter;

the first optical filter and second optical filter transmit light of mutually different wavelengths; and the emission wavelength switching part places the first optical filter and second optical filter on the optical path of the light emitted from the light source in sequence.

10. The sample analyzer of claim 3, wherein:

the light source comprises a first light emitting element for emitting light of a first wavelength, and a second light emitting element for emitting light of a second wavelength; and the emission wavelength switching part controls the first light emitting element and the second light emitting element so that the first light emitting element and the second light emitting element emit light sequentially.

11. The sample analyzer of claim 1, wherein the light source section has a light collecting part for collecting and guiding the light emitted from the light source to the first light guide and the second light guide.

12. The sample analyzer of claim 1, wherein:

each of the container holding sections further comprising a photoreceptor element, and the photoreceptor element detects the intensity of the light obtained from the sample container accommodating the measurement specimen.

13. The sample analyzer of claim 1, wherein:

the second optical information acquiring section comprises a reference light monitoring section for monitoring the characteristics of the light supplied from the light source; and the second light guide further comprises an additional branch which is connected to the reference light monitoring section whereby light is supplied from the light source to the reference light monitoring section.

14. The sample analyzer of claim 13, wherein the reference light monitoring section further comprises a photoreceptor which detects the intensity of the light supplied from the light source to the reference light monitoring section via the additional branch.

15. A sample analyzing method, intended for use in a sample analyzer of claim 1, comprising:

(a) providing a sample container accommodating a sample on an annular table for transporting the sample container;

(b) illuminating the sample in the sample container on the annular table with light emitted from a light source by using a light emitting device which has the light source, and acquiring first optical information from the sample;

(c) preparing a measurement specimen by adding a reagent to the sample;

(d) illuminating the measurement specimen with light emitted from the light source by using the light emitting device, and acquiring second optical information from the measurement specimen, wherein the measurement specimen is accommodated in a measurement specimen container;

(e) conducting an analysis of the characteristic of the sample based on the first optical information and second optical information; and (f) outputting a result of the analysis.

16. The sample analyzer of claim 1, further comprising a second annular table for transporting the measurement specimen container, wherein the measurement specimen is prepared in the measurement specimen container on the second annular table.

17. The sample analyzer of claim 16, wherein the annular table and the second annular table are arranged coaxially.

18. The sample analyzer of claim 17, wherein the annular table is disposed on the outer side of the second annular table.

19. The sample analyzer of claim 16, further comprising a transporter for transporting the measurement specimen container from the second annular table to the second optical information acquiring section.

20. A sample analyzer comprising:

a sample container accommodating a sample;

a light source section for emitting light;

a first optical information acquiring section for illuminating the sample in the sample container with the light emitted by the light source section, and for acquiring first optical information; and a second optical information acquiring section for illuminating a measurement specimen prepared by adding a reagent to the sample, with the light emitted by the light source section, and for acquiring second optical information, wherein the second optical information acquiring section is so configured that a measurement specimen container accommodating the measurement specimen is set thereon;

wherein the light source section comprises;

a light source;

a first light guide for guiding light emitted from the light source to the sample in the first optical information acquiring section; and a second light guide for guiding light emitted from the light source to the measurement specimen in the second optical information acquiring section; and wherein the second optical information acquiring section has a plurality of container holding sections for holding specimen containers that accommodate measurement specimens;

the second light guide has a plurality of branches;

the branches are connected to the container holding sections; and light is supplied from the light source to the plurality of container holding sections.

21. A sample analyzing method, intended for use in a sample analyzer of claim 20, comprising:

(a) providing a sample container accommodating a sample for transporting the sample container;

(b) illuminating the sample in the sample container with light emitted from a light source by using a light emitting device which has the light source, and acquiring first optical information from the sample;

(c) preparing a measurement specimen by adding a reagent to the sample;

(d) illuminating the measurement specimen with light emitted from the light source by using the light emitting device, and acquiring second optical information from the measurement specimen, wherein the measurement specimen is accommodated in a measurement specimen container;

(e) conducting an analysis of the characteristic of the sample based on the first optical information and second optical information; and (f) outputting a result of the analysis.

* * * * *